US010836731B2

(12) United States Patent
Pasquinet et al.

(10) Patent No.: US 10,836,731 B2
(45) Date of Patent: Nov. 17, 2020

(54) PRECIPITATION METHOD AND SYNTHESIS METHOD OF 2,6-DIAMINO-3,5-DINITROPYRAZINE-1-OXIDE

(71) Applicant: COMMISSARIAT A L'ÉNERGIE ATOMIQUE ET AUX ÉNERGIES ALTERNATIVES, Paris (FR)

(72) Inventors: Eric Pasquinet, Siant-Avertin (FR); Anne Wuillaume, Tours (FR); Nicolas Pin, Jou-les-Tours (FR); Arnaud Beaucamp, Neuil (FR); Christelle Barthet, Artannes-sur-Indre (FR)

(73) Assignee: COMMISSARIAT A L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/488,056

(22) PCT Filed: Feb. 26, 2018

(86) PCT No.: PCT/EP2018/054632
§ 371 (c)(1),
(2) Date: Aug. 22, 2019

(87) PCT Pub. No.: WO2018/158177
PCT Pub. Date: Sep. 7, 2018

(65) Prior Publication Data
US 2020/0010431 A1  Jan. 9, 2020

Related U.S. Application Data

(60) Provisional application No. 62/552,762, filed on Aug. 31, 2017.

(30) Foreign Application Priority Data

Feb. 28, 2017 (FR) .................................... 17 51645

(51) Int. Cl.
*C07D 241/20* (2006.01)
*B01D 9/00* (2006.01)
(52) U.S. Cl.
CPC .......... *C07D 241/20* (2013.01); *B01D 9/005* (2013.01); *B01D 2009/009* (2013.01); *C07B 2200/13* (2013.01)

(58) Field of Classification Search
CPC .................................................... C07D 241/20
See application file for complete search history.

(56) References Cited

U.S. PATENT DOCUMENTS

2009/0299067 A1   12/2009   Pagoria et al.

FOREIGN PATENT DOCUMENTS

| CN | 104693130 A | 6/2015 |
| CN | 104892531 A | 9/2015 |
| CN | 105503750 A | 4/2016 |
| WO | 2010123806 A1 | 10/2010 |

OTHER PUBLICATIONS

Search Report for French application No. 1751645 dated Nov. 10, 2017.
International Search Report for PCT/EP2018054632 dated Oct. 1, 2018.
Written Opinion for PCT/EP2018054632 dated Oct. 1, 2018.
Tran. T.D., et al. Small-Scale Safety and Performance Characterization of New Plastic Bonded Explosives Containing LLM-105, IN: 12th Internatioanl Detonation Symposium, Aug. 11-16, 2002.
Zuckerman, N.B. et al. "Microreactor Flow Synthesis of the Secondary High Explosive 2,6-Diamino-3,5-dinitropyrazine-1-oxide(LLM-105)" IN: Intensive Munitions & Energetic Materials Technology Symposium, May 18-21, 2015.
Ende, D. am et al. "Morphology Study" N: Intensive Munitions & Energetic Materials Technology Symposium, May 18-21, 2015.
Lemoine, D. et al. "Réactivité d'explosifs fortement confinés soumis à un chauffage lent" IN: EUROPYRO Jun. 5-9, 1995.
Reynier, P. "Saftey test for explosives densification" IN: Joint International Symposium on Energetic Materials Technology, Oct. 5-7, 1992.

*Primary Examiner* — Paul V Ward
(74) *Attorney, Agent, or Firm* — Pearne & Gordon LLP

(57) ABSTRACT

A method for precipitating as particles 2,6-diamino-3,5-dinitropyrazine-1-oxide (or ANPZO) present in an acid medium, which comprises adding the acid medium to an aqueous solution and which is characterized in that the aqueous solution comprises a nitrate salt. Further disclosed is a method for synthesizing ANPZO implementing this precipitation method. The synthesis method comprises converting 2,6-diaminopyrazine-1-oxide (or DAPO) into ANPZO by nitration in an acid medium, and then precipitating as particles the ANPZO by adding the acid medium to an aqueous solution, and is characterized in that the aqueous solution comprises a nitrate salt.

17 Claims, 5 Drawing Sheets

PRECIPITATION METHOD AND SYNTHESIS METHOD OF 2,6-DIAMINO-3,5-DINITROPYRAZINE-1-OXIDE

CROSS-REFERENCE TO RELATED APPLICATIONS

This is a National Stage application of PCT international application PCT/EP2018/054632, filed on Feb. 26, 2019, which claims the priority of French Patent Application No. 17 51645, filed Feb. 28, 2017 and U.S. provisional application No. 62/552,762, filed Aug. 31, 2017, all of which are incorporated herein by reference in their entireties.

TECHNICAL FIELD

The invention relates to the field of preparation of 2,6-diamino-3,5-dinitropyrazine-1-oxide (CAS 194486-77-6), further known under the names of ANPZO, LLM-105, NPEX-1, PZO and DDPO, and more simply named as ANPZO in the following.

More specifically, it relates to a method for precipitating ANPZO as particles as well as to a method for synthesizing ANPZO implementing this precipitation method.

Prior Art

ANPZO is an explosive which has an excellent compromise between energy performances and safety constraints (unsensitivity to shock, to sparks and friction, thermal stability, etc), which makes it a compound of interest in the field of energy materials.

Essentially there are two synthesis routes for ANPZO:
a first route, called "DMP route", wherein ANPZO is synthesized from 2,6-dimethoxypyrazine (or DMP) and which comprises three successive chemical reactions, namely: a nitration of DMP for obtaining 2,6-dimethoxy-3,5-dinitropyrazine (or DMDNP), an amination of DMDNP for obtaining 2,6-diamino-3,5-dinitropyrazine (or ANPZ) and an oxidation of ANPZ for obtaining ANPZO (cf., for example, T. D. Tran et al., 12$^{th}$ International Detonation Symposium, Aug. 11-16, 2002, San Diego, USA, hereafter reference [1]); and
a second route, called "DAPO route", wherein ANPZO is directly obtained from 2,6-diaminopyrazine-1-oxide (or DAPO) by nitration of the latter by means of nitric acid and in the presence of sulfuric acid, and then precipitation of ANPZO resulting from this nitration.

The DAPO route, which was developed by the National Lawrence Livermore Laboratory (or LLNL), was initially proposed with a precipitation in water (cf. patent application US 2009/0299067), hereafter reference [2]), and then secondarily with a precipitation in a mixture of water and ice (cf. International PCT application WO 2010/123806, hereafter reference [3]).

As applied in reference [3], the DAPO route may be schematized as follows:

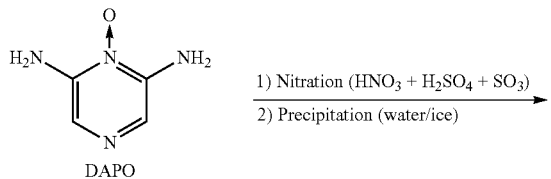

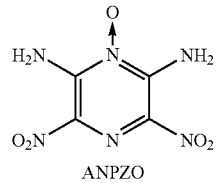

Relatively to the DMP route, the DAPO route has several advantages including that of comprising less reaction steps, of leading to an ANPZO of greater purity, of being less expensive and of involving any intermediate nitrated product and, therefore, potentially explosive, the only explosive product of the DAPO route being ANPZO itself.

On the other hand, unlike the DMP route which gives the possibility of obtaining particles of ANPZO in cubic form and for which the average size may range from 40 μm to 80 μm when the ANPZO is not re-crystallized (cf. reference [1]), the DAPO route as described in references [2] and [3] leads to ANPZO particles of diverse shape or in rods and of a very small size, typically less than 10 μm (cf. Zuckerman et al., Intensive Munitions & Energetic Materials Technology Symposium, May 18-21, 2015, Rome, Italy, hereafter reference [4]).

Now, it is known that particles of explosive with a high aspect ratio, i.e. of the type rods, needles, lamellas or the like, are not very adapted to the formulation of energy materials and it is preferable to operate with particles with a stronger shape isotropy and, ideally, of the cubic type which lend themselves more to a coating with a binder (cf., for example, D. am Ende et al., Insensitive Munitions & Energetic Material Technology Symposium, May 18-21, 2015, Rome, Italy, hereafter reference [5]).

Moreover, the finer are the particles of explosive, more their handling poses problems of working as well as of hygiene and safety notably because of an increased risk of formation of clouds of explosive dusts and inhalation of these dusts by the manipulators.

This explains that a certain number of studies were conducted with the purpose of improving both the morphology and the size of the particles of ANPZO obtained by the DAPO route, notably by acting on the precipitation conditions and in particular on the precipitation medium and temperature.

The results of these studies show that:
most organo-aqueous precipitation media (diluted formic acid, diluted dimethylformamide, diluted sulfolane, etc) lead, like the precipitation in water or in a water/ice mixture, to particles of ANPZO of a very small size in the form of rods or lamellas;
the use of a water heated to 40° C. as a precipitation medium gives the possibility of increasing the size of the particles of ANPZO but the particles are of an acicular shape; further, in this case, the differential scanning calorimetric analysis curve (or DSC thermogram "Differential Scanning calorimetry") of ANPZO has an exothermic peak at about 300° C. (therefore preceding the normal thermal decomposition peak of ANPZO which is located around 350° C.) and for which the presence indicates an insufficient purity of ANPZO; a recrystallization of ANPZO in a mixture of dimethylformamide and water is therefore necessary in order to obtain an ANPZO with a DSC thermogram according to the one which ANPZO should exhibit (cf. reference [5]); while the concentrated acids are precipitation media which have the most impact on the morphology of the particles of ANPZO with however heterogeneous results; thus, the hydrochloric and trifluoroacetic acids lead to particles of ANPZO with a high form factor while formic acid gives the possibility of obtaining the greatest number of ANPZO particles of the cubic type; however, the size of these particles remains moderate since they have an median size (d0.5) of the order of 17 μm (cf. reference [5]); furthermore, the use of a concentrated acid in addition to that of concentrated nitric and sulfuric acids already made necessary by the nitration of DAPO is not desirable for reasons of handling the effluents.

Taking into account the foregoing, the inventors set their goal of managing to synthesize by the DAPO route particles of ANPZO for which the morphology and the size get closer at best to those which the particles of ANPZO obtained by the DMP route exhibit, while having a high degree of purity and a high thermal stability.

They also set their goal that this synthesis is simple to apply and does not require the use of reagents which may burden substantially the handling of the effluents of the DAPO route as proposed in references [2] and [3].

Now, within the scope of their studies, the inventors ascertained that, unexpectedly, the use of an aqueous solution comprising a nitrate salt as a precipitation medium for ANPZO when the latter is present in an acid medium such as a sulfonitric medium, gives the possibility of obtaining particles of ANPZO which meet all the sought criteria of morphology, size, purity and thermal stability.

And the invention is based on these experimental observations.

DISCUSSION OF THE INVENTION

The invention relates therefore to a method for precipitating as particles ANPZO present in an acid medium comprising nitric acid or a nitrate salt or a mixture thereof, and at least one strong acid other than nitric acid, which precipitation method comprises adding the acid medium to an aqueous solution and is characterized in that the aqueous solution comprises a nitrate salt.

The invention also relates to a method for synthesizing ANPZO implementing this precipitation method, which synthesis method comprises:
converting DAPO into ANPZO by nitration in an acid medium which comprises nitric acid or a nitrate salt or a mixture thereof, and at least one strong acid other than nitric acid, and then
precipitating as particles ANPZO by addition of the acid medium to an aqueous solution,
and is characterized in that the aqueous solution comprises a nitrate salt.

In the foregoing and in the following, by "strong acid" is meant any acid which is conventionally defined as such in the field of chemistry, i.e. any acid which totally dissociates in water according to the reaction: $HA + H_2O \rightarrow H_3O^+ + A^-$. The pKa of such an acid is therefore less than the pKa of the hydronium ion $H_3O^+$, i.e. less than −1.7.

According to the invention, the nitrate salt of the aqueous solution may be:
a nitrate with a metal cation such as a nitrate of an alkaline metal, for example sodium nitrate ($NaNO_3$), potassium nitrate ($KNO_3$), lithium nitrate ($LiNO_3$) or cesium nitrate ($CsNO_3$) or of an earth-alkaline metal, for example calcium nitrate ($Ca(NO_3)_2$) or magnesium nitrate ($Mg(NO_3)_2$), or a nitrate with a non-metal cation such as ammonium nitrate ($NH_4NO_3$), guanidinium nitrate ($[C(NH_2)_3]NO_3$) or aminoguanidinium nitrate.

Preferably, the nitrate salt of the aqueous solution is selected from sodium nitrate, potassium nitrate and ammonium nitrate.

The amount of the nitrate salt in the aqueous solution may vary in a wide range, typically from 110 g to 2,500 g for 1 L of water, a range in which this amount may advantageously be selected according to the size which one intends to give to the particles of ANPZO.

Indeed, the Inventors have found that, for concentrations of ANPZO in the acid medium identical or quasi-identical and for ratios between the volume of the aqueous solution comprising the nitrate salt and the volume of the acid medium comprising ANPZO identical or quasi-identical, the median size of the particles of ANPZO is all the higher if the amount of nitrate salt in the aqueous solution is higher, and that, without any significant impact on the other properties of ANPZO.

It is therefore possible to act on the amount of the nitrate salt present in the aqueous solution for modulating the median size of the particles of ANPZO.

According to the invention, the ratio of the volume of the aqueous solution comprising the nitrate salt to the volume of the acid medium which is added to it is advantageously comprised between 0.5 and 10 and, even better, between 2 and 6.

The addition of the acid medium to the aqueous solution comprising the nitrate salt is preferably achieved gradually, in which case it may be achieved either by portions, i.e. in a fractionated way, or continuously, for example by means of a conduit under control of a pump.

According to the invention, the precipitation of ANPZO as particles is advantageously completed with:
a collection of the particles, for example by filtration of the medium resulting from the addition of the acid medium to the aqueous solution comprising the nitrate salt;
a washing of the thereby collected particles, which washing may comprise a series of washing operations such as for example one or several washing operations with water at room temperature and/or with a basic solution such as a sodium carbonate or bicarbonate solution for neutralizing the acidity of the particles and/or with an organic solvent such as methylethylketone, optionally mixed with water, and/or with water heated to a temperature comprised between 50° C. and 100° C.; and
a drying of the thereby washed particles, for example by heating in vacua.

As to the conversion of DAPO into ANPZO by nitration in acid medium, it preferentially comprises:
forming a reaction medium by adding nitric acid or a nitrate salt to a solution comprising the DAPO, at a concentration typically comprised between 40 g/L and 150 g/L, in a strong acid other than nitric acid, and
maintaining the reaction medium under stirring, for example for 1 hour to 20 hours, preferably at room temperature.

According to the invention, the acid medium is preferably a sulfonitric medium, i.e. a medium which comprises sulfuric acid ($H_2SO_4$) as a strong acid other than nitric acid. This medium may optionally comprise additionally sulfur trioxide ($SO_3$) if the sulfuric acid is used totally or partly the form of an oleum (or fuming sulfuric acid) as described in references [2], [3] and [4].

However, it is also possible to use instead of sulfuric acid or in a mixture with sulfuric acid, another strong acid such as trifluoroacetic acid ($CF_3COOH$), methanesulfonic acid ($CH_3SO_3H$), trifluoromethanesulfonic acid ($CF_3SO_3H$), further known as triflic acid, or a heteropolyacid like phosphotungstic acid, silicotungstic acid, phosphomolybdic acid or tungstomolybdic acid.

In a preferred way among all ways, the acid medium comprises nitric acid and sulfuric acid.

In which case, for the conversion of DAPO into ANPZO, nitric acid with a concentration at least equal to 90%, sulfuric acid with a concentration comprised between 95% and 98% and a ratio of the volume of nitric acid to the volume of the sulfuric solution comprising the DAPO comprised between 0.1 and 0.2 are preferentially used.

However, it is obvious that this conversion may also be achieved by replacing notably a portion of the sulfuric acid with an oleum, for example at 20% and/or by replacing all or part of the nitric acid by a nitrate salt, for example a sodium, potassium or ammonium nitrate.

The invention has many advantages.

Indeed, as demonstrated in the following examples, it gives the possibility of obtaining via the DAPO route particles of ANPZO which have both an aspect ratio (i.e. a ratio of the maximum Féret diameter to the minimum Féret diameter) of no more than 2 and, typically, of no more than 1.4, a median size (d0.5) by volume, as determined by laser diffraction particle size measurement, at least equal to 35 µm and which may exceed 60 µm, a purity degree of more than 99.5% and this, without resorting to a subsequent crystallization (simple washing operations of the particles are sufficient), as well as a high thermal stability with an initial temperature of thermal decomposition around 350° C.

As also demonstrated in the following examples, it gives the possibility of further modulating the median size of the particles of ANPZO if this is desired, which is interesting in the case when an energy material is intended to be formulated from several batches of ANPZO with different median particle sizes.

Further, it is simple to implement (the precipitation of ANPZO being achieved only in a single step) and requires, relatively to the DAPO route as initially proposed in references [2] and [3], only the use of one additional reagent which is a nitrate salt and which does not pose any particular problems in the handling method of the effluents since the nitrate effluents may actually be easily rid of the nitrates which they contain by denitration by means of an ion exchange resin, by biological treatment of denitrification or by membrane filtration.

Other features and advantages of the invention will emerge from the additional description which follows and which relates to examples of synthesis of ANPZO by the synthesis method of the invention and of characterization for the properties of the thereby synthesized ANPZO.

It is obvious that this additional description is only given as an illustration of the object of the invention and should by no means be interpreted as a limitation of this object.

SHORT DESCRIPTION OF THE FIGURES

DETAILED DISCUSSION OF PARTICULAR EMBODIMENTS

Preliminary Remarks:

The SEM images which are shown in FIGS. 1 to 3, 5 and 7 to 10 were obtained with a scanning electron microscope FEI Versa 3D, at a magnification of 500.

Figure 4:
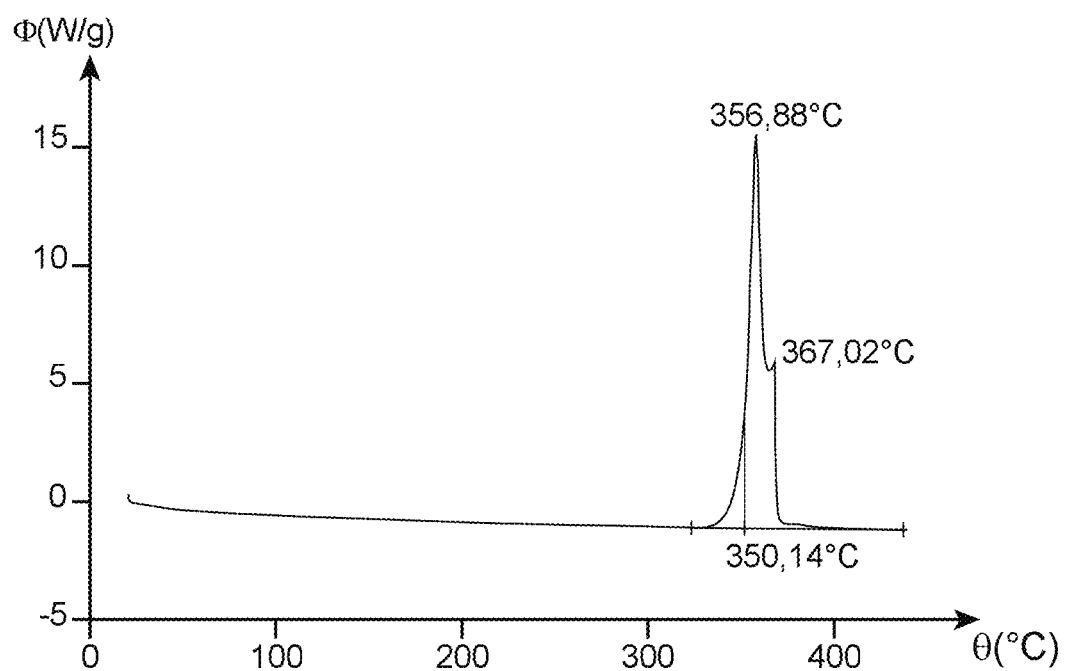
FIG. 4 illustrates the DSC thermogram for the ANPZO, the particles of which are shown in FIG. 3; the heat flux, noted as Φ and expressed in W/g, is indicated on the axis of ordinates, while the temperature, noted as θ and expressed in ° C. is indicated on the axis of abscissas.

The DSC thermogram which is shown in FIG. 4 as well as the initial decomposition temperatures (or $θ_{onset}$) which are indicated in table 1 hereafter were obtained with a calorimeter TA Instruments Q100 (heating rate: 10° C./min).

Figure 6:
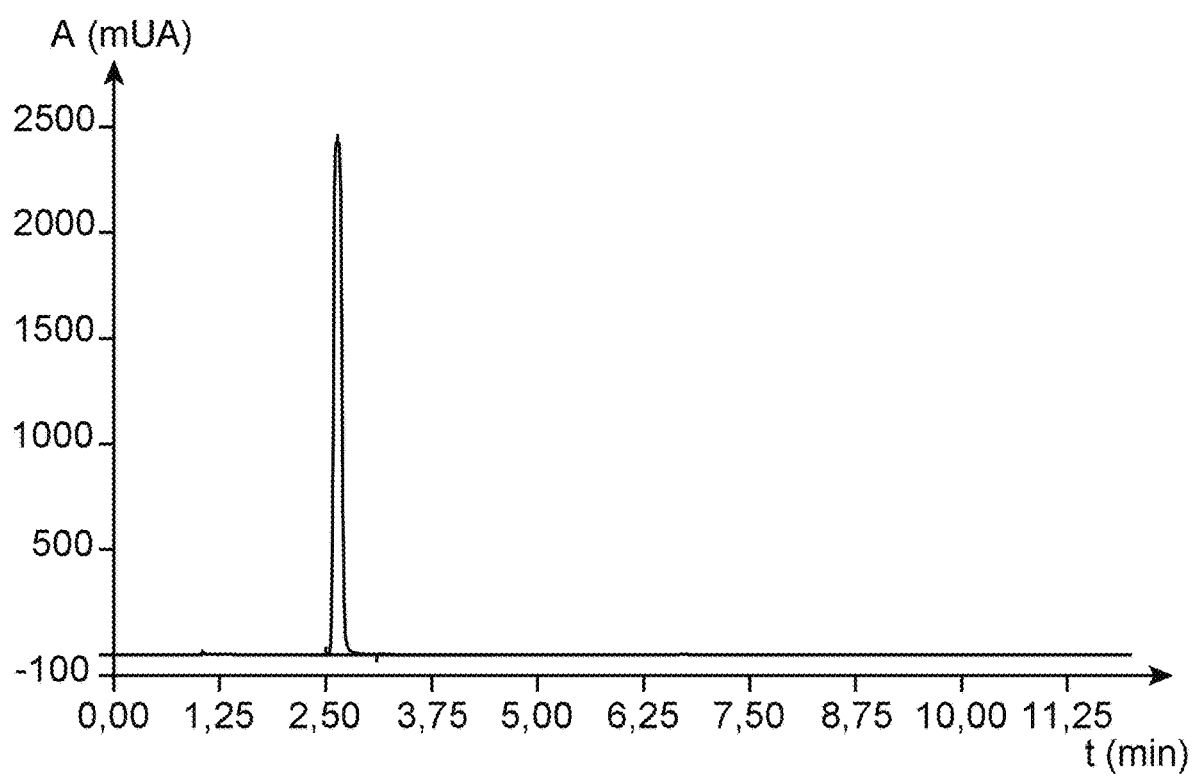
FIG. 6 is the chromatogram obtained by high performance liquid chromatography (or HPLC) for the ANPZO, the particles of which are shown in FIG. 5; the absorbance, noted as A and expressed in milli-units of absorbance (mUA), is indicated on the axis of the ordinates, while the time, noted as t and expressed in minutes, is indicated on the axis of the abscissas.

The HPLC chromatogram which is shown in FIG. 6 was obtained by using a column Kinetex™ C18 (Phenomenex SAS) and UV detection at 320 nm.

The sizes of the particles which are indicated in table 1 hereafter were measured by laser diffraction particle size measurements with a granulometer Malvern Mastersizer S (lens 300 RF; 0.1-900 µm). The measurements were conducted via a liquid route (water without any surfactant) and with dispersion by treatment with ultrasonic waves. On the one hand, the main modes, i.e. the sizes where the maximum frequencies of the granulometric histograms are located (the distributions being monomodal), and, on the other hand, the median sizes (d0.5) by volume are indicated in table 1. To the extent that the ANPZO particles are not spheres, these sizes correspond to the diameters which spheres having the same volume as these particles would have.

The stability values in vacuo at 140° C. which are indicated in table 1 hereafter were measured by subjecting samples of ANPZO to a heating to 140° C. in vacuo for 70 hours and by measuring the total released gas volume (expressed at a pressure of 1,013 hPa and at a temperature of 0° C.) by these samples during the heating period. They are expressed in cm³ per gram of sample. The test sample is 5 g.

The rates of volatile materials on dry product which are indicated in table 1 hereafter were measured by subjecting the dry ANPZO samples to heating at 120° C. in an oven for 16 hours. They are expressed in percentages obtained by the formula: [(mass before test–mass after test)/mass before test]×100. The test sample is 5 g.

The residual nitrate ion contents (or $Q_{NO_3^-}$) which are indicated in table 1 hereafter were determined by nuclear magnetic resonance (or NMR) with a spectrometer Advance Bruker WB (400 MHz; probe 10 mm in $^{14}N$). They are expressed in mass percentages obtained by the formula $12600*(I_{NO_3^-}/I_{N_2})*[N_{2eq}]*f/[ANPZO]$ wherein $I_{NO_3^-}/I_{N_2}$ is the intensity ratio between the $NO_3^-$ line and the $N_2$ line; $[N_{2eq}]$ is the equilibrium concentration of $N_2$ in dimethylsulfoxide in mmol/L; f is a corrective factor and [ANPZO] is the concentration of ANPZO in the sample in mg/L.

The elemental analyses for which the results are indicated in table 1 hereafter were conducted with an elemental analyzer Flash EA 1112 (Thermofischer Scientific).

The thermomechanical tests for which the results are indicated in table 1 hereafter were conducted by means of a device called "a press with limits". This device, which is notably described in D. Lemoine et al., *Europyro* 1995, Jun. 5-9, 1995, Tours, France, and in P. Reynier, *Joint International Symposium on Energetic Materials Technology*, Oct. 5-7, 1992, New Orleans, USA, hereafter references [6] and [7], gives the possibility of evaluating the reactive behavior of an energy material subject to heating in a confined medium. Thus are measured: 1) the temperature, noted as $\theta_{decomp.}$ in table 1, at which a sample of ANPZO is broken down when it is subject to a pressure of 500 bars (temperature rise ramp: 2° C./min), and 2) the time, noted as $t_{decomp}$ in table 1, at the end of which a sample of ANPZO is broken down at 220° C. under a pressure of 500 bars.

Example 1: Synthesis of ANPZO by the Synthesis Method of the Invention

In a flask provided with a thermometer and a stirrer, 960 mL of sulfuric acid concentrated to 95-98% and then 112.9 g of DAPO portionwise are introduced. After dissolution of the DAPO dissolved in the sulfuric medium, 169.4 g of nitric acid concentrated to 99% are added slowly while maintaining the flask at a temperature below 35° C. The reaction medium is left under stirring for 2 hours, at room temperature.

This reaction medium is then added portionwise to 3.35 L of an aqueous solution comprising 600 g of ammonium nitrate for 1 L of water while maintaining the temperature of the flask at 30° C.

A precipitate is formed which is recovered by filtration and which is washed on the filter with water and then with an aqueous solution saturated with sodium bicarbonate (NaHCO₃) and then again with water.

Thus 95 g of humid ANPZO are obtained which are divided into two batches:
  a first batch—hereafter batch 1—which is dried without subjecting it to additional washing, whereby 38.08 g of dry ANPZO are obtained, and
  a second batch—hereafter batch 2—which is subject to two additional washings, the first with water at 80° C. and the second with a water/methylethylketone mixture (1/9, v/v) at 75° C., before drying it, whereby 50.42 g of dry ANPZO are obtained.

The yield of this synthesis is 46% (88.5 g).

The batches 1 and 2 of ANPZO are subject to a series of analyses: SEM, DSC, particle size analyses, measurement of the stability in vacuo at 140° C., measurement of the volatile material rate on dry product, measurement of the residual nitrate content, elemental analyses and thermomechanical tests.

Figure 1:
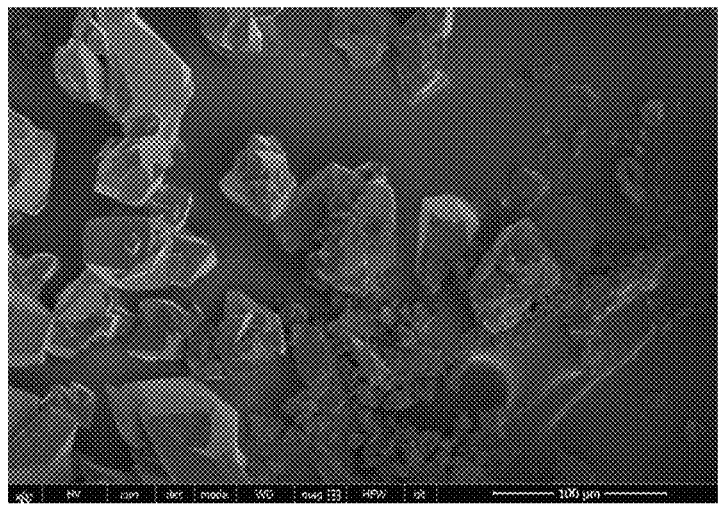
FIG. 1 is an image taken with a scanning electron microscope (or SEM) showing the particles of a first ANPZO synthesized by the synthesis method of the invention.
Figure 2:
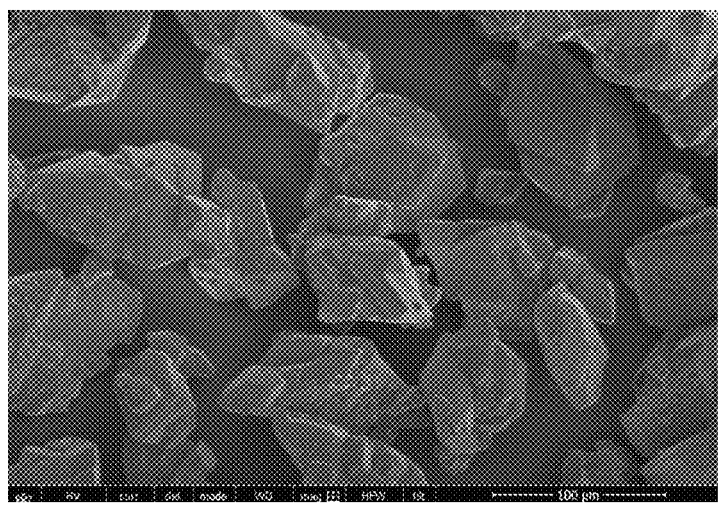
FIG. 2 is an SEM image showing the particles of a second ANPZO synthesized by the synthesis method of the invention.

The SEM images showing particles of both of these batches of ANPZO are illustrated in FIGS. 1 and 2 respectively, while the results of the other analyses are indicated in table 1 hereafter.

Example 2: Synthesis of ANPZO by the Synthesis Method of the Invention

In a flask provided with a thermometer and a stirrer, 3.84 L of sulfuric acid concentrated to 95-98% and then 452.2 g of DAPO portionwise are introduced. After dissolution of the DAPO in the sulfuric medium, 678.8 g of nitric acid concentrated to 99% are slowly added while maintaining the flask at a temperature below 35° C. The reaction medium is left under stirring for 2 hours at room temperature.

This reaction medium is then added portionwise to 12.9 L of an aqueous solution comprising 600 g of ammonium nitrate for 1 L of water while maintaining the temperature of the precipitation medium around 30° C.

A precipitate is formed which is recovered by filtration and which is washed on the filter with water and then with an aqueous solution saturated with NaHCO₃ and then again with water.

The thereby obtained humid ANPZO is subject to two additional washes, the first with water at 80° C. and the second with a water/methylethylketone mixture (1/9, v/v) at 75° C., and then to a drying, whereby 342 g of dry ANPZO are obtained (yield: 44%).

This ANPZO is subject to a series of analyses: SEM, DSC, particle size analyses, measurement of the stability in vacuo at 140° C., measurement of the volatile material rate on dry product, measurement of the residual nitrate content, elemental analyses and thermomechanical tests.

Figure 3:
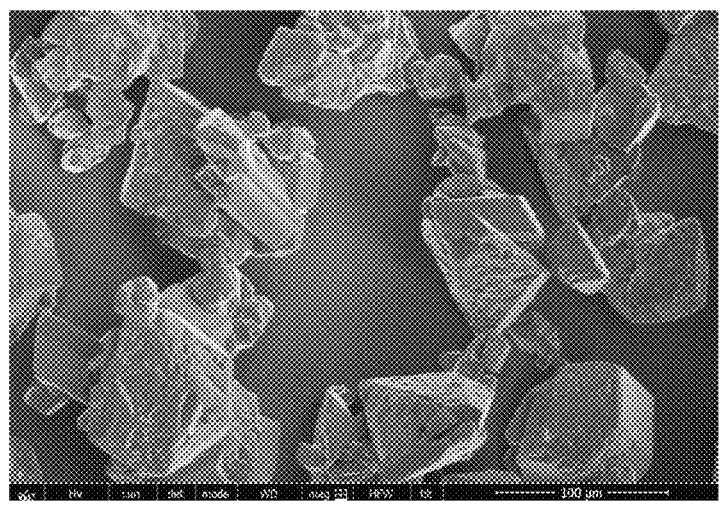
FIG. 3 is an SEM image showing the particles of a third ANPZO synthesized by the synthesis method of the invention.

The SEM image showing the particles of this ANPZO is illustrated in FIG. 3. Its thermogram is illustrated in FIG. 4 while the other analyses are indicated in table 1 hereafter.

Example 3: Synthesis of ANPZO by the Synthesis Method of the Invention

The same operating protocol as the one described in Example 2 hereinbefore is followed except that the humid ANPZO is only subject to a single additional wash (instead of two), i.e. the wash with water at 80° C., whereby 356 g of dry ANPZO are obtained (yield: 46%).

This ANPZO is subject to a series of analyses: SEM, DSC, particle size analyses, measurement of the stability in vacuo at 140° C., measurement of the volatile material rate on dry product, measurement of the residual nitrate content, elemental analyses and thermomechanical tests. It is further subject to a HPLC chromatography.

Figure 5:
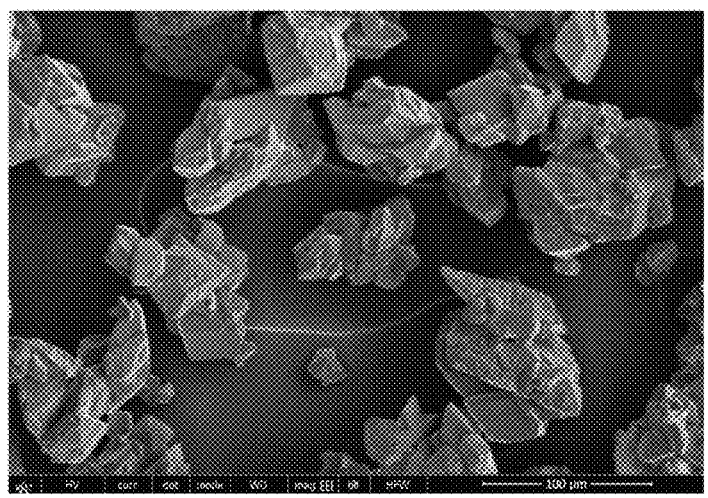
FIG. 5 is an SEM image showing the particles of a fourth ANPZO synthesized by the synthesis method of the invention.

The SEM image showing the particles of this ANPZO is illustrated in FIG. 5. Its HPLC chromatogram is illustrated in FIG. 6, while the results of the other analyses are indicated in table I hereafter.

Example 4: Synthesis of ANPZO by the Synthesis Method of the Invention

In a flask provided with a thermometer and a stirrer, 4.9 L of sulfuric acid concentrated to 95-98% and then 577.3 g of DAPO portionwise are introduced. After dissolution of the DAPO in the sulfuric medium, 865.5 g of nitric acid concentrated to 99% are slowly added while maintaining the flask at a temperature below 35° C. The reaction medium is left with stirring for 2 hours, at room temperature.

This reaction medium is then added portionwise to 17.1 L of an aqueous solution comprising 250 g of ammonium nitrate for 1 L of water while maintaining the temperature of the precipitation medium around 30° C.

A precipitate is formed which is recovered by filtration and which is washed on the filter with water and then with an aqueous solution saturated with $NaHCO_3$ and then again with water.

The thereby obtained humid ANPZO is subject to an additional wash with water at 80° C., and then to a drying, whereby 474 g of dry ANPZO are obtained (yield: 48%).

This ANPZO is subject to a series of analyses: SEM, DSC, particle size analyses, measurement of the stability in vacuo at 140° C., measurement of the volatile material rate on dry product, measurement of the residual nitrate content, elemental analyses and thermomechanical tests.

Figure 7:
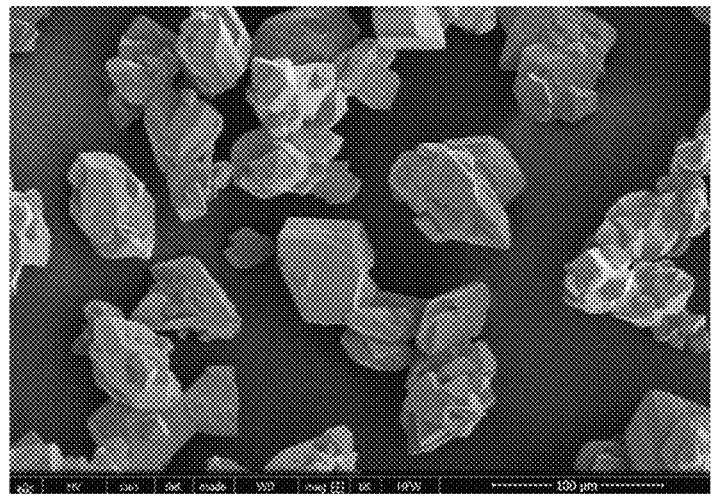
FIG. 7 is an SEM image showing the particles of a fifth ANPZO synthesized by the synthesis method of the invention.

The SEM image showing the particles of this ANPZO is illustrated in FIG. 7 while the results of the other analyses are indicated in table I hereafter.

Example 5: Synthesis of ANPZO by the Synthesis Method of the Invention

In a flask provided with a thermometer and a stirrer, 3.84 L of sulfuric acid concentrated to 95-98% and then 452.2 g of DAPO portionwise are introduced. After dissolution of the DAPO in the sulfuric medium, 678 g of nitric acid concentrated to 99% are slowly added while maintaining the flask at a temperature below 35° C. The reaction medium is left with stirring for 2 hours, at room temperature.

This reaction medium is then added portionwise to 13.4 L of an aqueous solution comprising 260 g of potassium nitrate for 1 L of water while maintaining the temperature of the precipitation medium around 30° C.

A precipitate is formed which is recovered by filtration and which is washed on the filter with water and then with an aqueous solution saturated with $NaHCO_3$ and then again with water.

The thereby obtained humid ANPZO is subject to an additional wash with water at 80° C., and then to a drying, whereby 340 g of dry ANPZO are obtained (yield: 44%).

This ANPZO is subject to series of analyses: SEM, DSC, particle size analyses, measurement of the stability in vacua at 140° C., measurement of the volatile material rate on dry product, measurement of the residual nitrate content, elemental analyses and thermomechanical tests.

Figure 8:
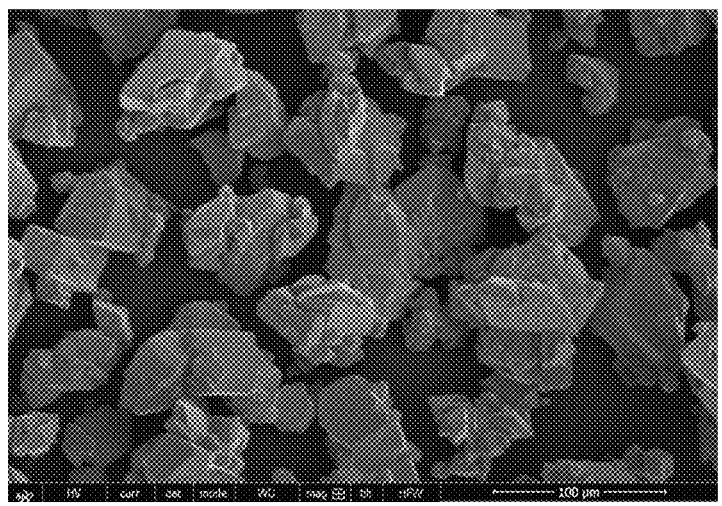
FIG. 8 is an SEM image showing the particles of a sixth ANPZO synthesized by the synthesis method of the invention.

The SEM image showing the particles of this ANPZO is illustrated in FIG. 8 while the results of the other analyses are indicated in table 1 hereafter.

Example 6: Synthesis of ANPZO by the Synthesis Method of the Invention

In a flask provided with a thermometer and a stirrer, 3.84 L of sulfuric acid concentrated to 95-98% and then 452.2 g of DAPO portionwise are introduced. After dissolution of the DAPO in the sulfuric medium, 678 g of concentrated nitric acid to 99% are slowly added while maintaining the flask at a temperature below 35° C. The reaction medium is left under stirring for 2 hours at room temperature.

This reaction medium is then added portionwise to 13.4 L of an aqueous solution comprising 570 g of sodium nitrate for 1 L of water while maintaining the temperature of the precipitation medium around 30° C.

A precipitate forms which is recovered by filtration and which is washed on the filter with water and then with an aqueous solution saturated with $NaHCO_3$ and then again with water.

The thereby obtained humid ANPZO is subject to an additional wash with water at 80° C., and then to a drying, whereby 366 g of dry ANPZO are obtained (yield: 47%).

This ANPZO is subject to a series of analyses: SEM, DSC, particle size analyses, measurement of the stability in vacuo at 140° C., measurement of the volatile material rate on dry product, measurement of the residual nitrate content, elemental analyses and thermomechanical tests.

Figure 9:
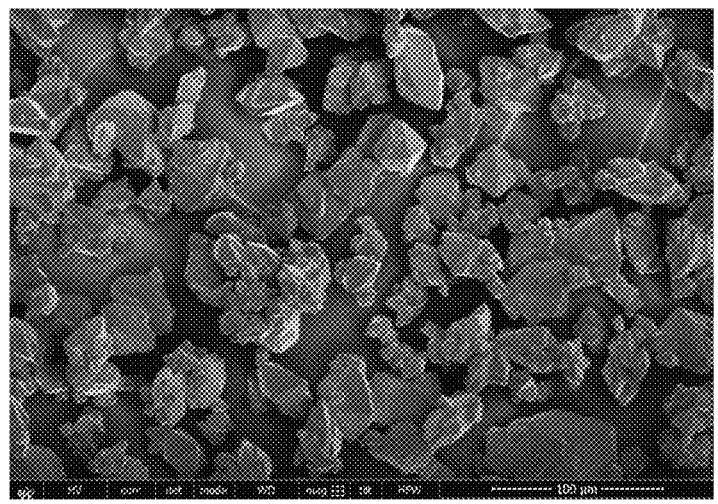
FIG. 9 is an SEM image showing the particles of a seventh ANPZO synthesized by the synthesis method of the invention.

The SEM image showing particles of this ANPZO is illustrated in FIG. 9 while the results of the other analyses are indicated in table 1 hereafter.

Example 7: Comparative Example

In a flask provided with a thermometer and a stirrer, 3.84 L of concentrated sulfuric acid and then 451.9 g of DAPO portionwise are introduced. After dissolution of the DAPO in the sulfuric medium, 678 g of concentrated nitric acid are slowly added while maintaining the flask at a temperature below 35° C. The reaction medium is left under stirring for 2 hours, at room temperature.

This reaction medium is then added portionwise to 13.4 L of water while maintaining the temperature of the flask at 30° C.

A precipitate is formed which is recovered by filtration and which is washed on the filter with water and then with an aqueous solution saturated with $NaHCO_3$ and then again with water.

The thereby obtained humid ANPZO is subject to an additional wash with water at 80° C. and then to a drying, whereby 401 g of dry ANPZO are obtained (yield: 52%).

This ANPZO is subject to a series of analyses: SEM, DSC, particle size analyses, measurement of the stability in vacuo at 140° C., measurement of the volatile material rate on dry product, measurement of the residual nitrate content, elemental analyses and thermomechanical tests.

Figure 10:
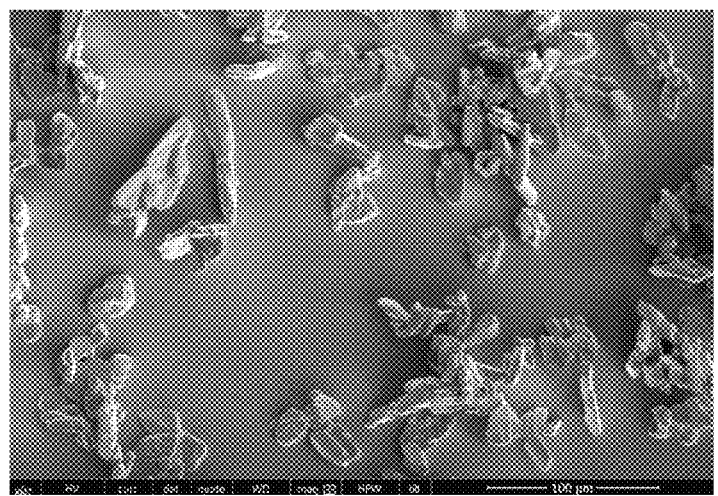
FIG. 10 is an SEM image showing as a comparison the particles of a eighth ANPZO synthesized by a synthesis method which differs from the synthesis method of the invention in that the precipitation of ANPZO was achieved by addition of a sulfonitric medium comprising ANPZO in water at 30° C.

The SEM image showing the particles of this batch is illustrated in FIG. 10 while the results of the other analyses are indicated in table 1 hereafter.

TABLE I

| ANPZO | Main mode (μm) | d0.5 (μm) | $\theta_{onset}$ (°C) | Stability in vacuo at 140° C. (cm³/g) | Volatile material rate (%) | $Q_{NO3-}$ (%) | Elemental analyses* (% m/m) | | | | Thermomechanical tests | |
|---|---|---|---|---|---|---|---|---|---|---|---|---|
| | | | | | | | C | H | N | S | $\theta_{decomp.}$ 500 bars (° C.) | $t_{decomp.}$ 500 bars 220° C. (min) |
| Example 1: batch 1 | 71 | 66 | 350 | 0.05 | 0.04 | <0.05 | 22.2 | 1.8 | 38.2 | 0 | ND | 107 |
| Example 1: batch 2 | 71 | 59 | 350 | 0.04 | 0.01 | | 22.1 | 1.8 | 38.0 | | 261 | 67 |
| Example 2 | 62 | 56 | 350 | 0.07 | 0.06 | | 22.6 | 2.0 | 39.2 | | 246 | 54 |
| Example 3 | 62.5 | 59 | 349 | 0.06 | 0.07 | | 22.5 | 1.8 | 39.0 | | 270 | 50 |
| Example 4 | 52.5 | 49 | 349 | 0.05 | 0.04 | ND | 22.5 | 1.8 | 38.7 | | 260 | 54 |
| Example 5 | 60 | 56 | 347 | 0.05 | 0.05 | <0.05 | 22.4 | 1.7 | 38.2 | | 265 | 39 |
| Example 6 | 39 | 37 | 347 | 0.13 | 0.13 | | 22.3 | 1.8 | 38.5 | | 236 | 23 |
| Comparative example | 25 | 23 | 350 | 0.11 | 0.10 | | 22.4 | 1.8 | 38.4 | | 231 | 17 |

*Theory: C = 22.6%; H = 1.9%; N = 38.9%
ND = not determined

FIGS. 1 to 10 as well as this table show that the particles of synthesized ANPZO according to the invention have:
- an aspect ratio of no more than 2 and typically of no more than 1.4; and
- a median size (d0.5) by volume at least equal to 35 μm and which may attain 66 μm (cf. example 1, batch 2), while the median size by volume of the synthesized ANPZO particles in the comparative example is only 23 μm.

Table 1 also shows that these ANPZOs have:
- a high degree of purity objectified by their residual nitrate ion content which is less than 0.05%, by the mass percentages obtained for carbon, hydrogen, nitrogen and sulfur by the elemental analyses which are compliant with the theoretical percentages, as well as by the HPLC chromatogram of the ANPZO synthesized in example 3; and
- a high thermal stability objectified by their initial thermal decomposition temperature which is around 350° C.

Furthermore, it is noted an increase in their decomposition temperature under pressure as well as in the time required for their decomposition under pressure and at 220° C. relatively to those of the ANPZO particles synthesized in the comparative example, which increase is particularly marked when the nitrate salt is a potassium or ammonium nitrate.

QUOTED REFERENCES

[1] T. D. Tran et al., 12$^{th}$ International Detonation Symposium, Aug. 11-16, 2002, San Diego, USA
[2] Patent application US 2009/0299067
[3] International PCT application WO 2010/123806,
[4] Zuckerman et al., Intensive Munitions & Energetic Materials Technology Symposium, May 18-21, 2015, Rome, Italy
[5] D. am Ende et al., Insensitive Munitions & Energetic Material Technology Symposium, May 18-21, 2015, Rome, Italy
[6] D. Lemoine et al., Europyro 1995, Jun. 5-9, 1995, Tours, France
[7] P. Reynier, Joint International Symposium on Energetic Materials Technology, Oct. 5-7, 1992, New Orleans, USA

What is claimed is:

1. A method for precipitating as particles 2,6-diamino-3,5-dinitropyrazine -1-oxide present in an acid medium, the medium comprising nitric acid or a nitrate salt or a mixture thereof, and at least one strong acid other than nitric acid, the method comprising adding the acid medium to an aqueous solution comprising a nitrate salt; and precipitating as particles 2,6-diamino-3,5-dinitropyrazine-1-oxide.

2. A method for synthesizing particles of 2,6-diamino-3, 5-dinitropyrazine -1-oxide, comprising:
converting 2,6-diaminopyrazine-1-oxide into 2,6-diamino-3,5-dinitroyrazine-1-oxide by nitrating 2,6-diaminopyrazine-1-oxyde in an acid medium comprising nitric acid or a nitrate salt or a mixture thereof, and at least one strong acid other than nitric acid, and then
precipitating as particles 2,6-diamino-3,5-dinitropyrazine-1-oxide by adding the acid medium to an aqueous solution comprising a nitrate salt.

3. The method of claim 1, wherein the nitrate salt is sodium nitrate, potassium nitrate or ammonium nitrate.

4. The method of claim 1, wherein the aqueous solution comprises between 110 g and 2,500 g of the nitrate salt for 1 litre of water.

5. The method of claim 1, wherein a ratio of a volume of the aqueous solution to a volume of the acid medium is comprised between 0.5 and 10.

6. The method of claim 1, wherein the acid medium is gradually added to the aqueous solution.

7. The method of claim 1, further comprising collecting the particles, washing the particles and drying the particles.

8. The method of claim 2, wherein converting 2,6-diaminopyrazine -1-oxide into 2,6-diamino-3,5-dinitropyrazine-1-oxide comprises:
forming a reaction medium by adding nitric acid or a nitrate salt or a mixture thereof to a solution comprising 2,6-diaminopyrazine-1-oxide in at least one strong acid other than nitric acid; and
maintaining the reaction medium under stirring.

9. The method of claim 1, wherein the strong acid other than nitric acid is sulfuric acid.

10. The method according to claim 9, wherein the acid medium comprises nitric acid and sulfuric acid.

11. The method of claim 2, wherein the nitrate salt is sodium nitrate, potassium nitrate or ammonium nitrate.

12. The method of claim 2, wherein the aqueous solution comprises between 110 g and 2,500 g of the nitrate salt for 1 litre of water.

13. The method of claim 2, wherein a ratio of a volume of the aqueous solution to a volume of the acid medium is comprised between 0.5 and 10.

14. The method of claim 2, wherein the acid medium is gradually added to the aqueous solution.

15. The method of claim 2, further comprising collecting the particles, washing the particles and drying the particles.

16. The method of claim 2, wherein the strong acid other than nitric acid is sulfuric acid.

17. The method according to claim 16, wherein the acid medium comprises nitric acid and sulfuric acid.

* * * * *